(12) United States Patent
Eidenschink (10) Patent No.: US 6,783,542 B2
(45) Date of Patent: Aug. 31, 2004

(54) CRIMPABLE BALLOON/STENT PROTECTOR

(75) Inventor: Tracee E. J. Eidenschink, Wayzata, MN (US)

(73) Assignee: SciMed Life Systems, Inc, Maple Grove, MN (US)

( * ) Notice: Subject to any disclaimer, the term of this patent is extended or adjusted under 35 U.S.C. 154(b) by 57 days.

(21) Appl. No.: 09/790,967

(22) Filed: Feb. 22, 2001

(65) Prior Publication Data

US 2002/0116045 A1 Aug. 22, 2002

(51) Int. Cl.⁷ .................................................. A61F 2/06
(52) U.S. Cl. ........................ 623/1.11; 606/108; 606/195
(58) Field of Search .............................. 623/1.11, 1.12, 623/1.23; 606/108, 195, 1; 29/516

(56) References Cited

U.S. PATENT DOCUMENTS

| | | | | |
|---|---|---|---|---|
| 4,776,337 A | * | 10/1988 | Palmaz ........................ 128/343 |
| 5,817,100 A | * | 10/1998 | Igaki ............................ 606/108 |
| 5,992,000 A | * | 11/1999 | Humphrey et al. ............ 29/516 |
| 6,019,778 A | * | 2/2000 | Wilson et al. ............... 606/198 |
| 6,019,786 A | * | 2/2000 | Thompson ..................... 623/1 |
| 6,141,855 A | * | 11/2000 | Morales ........................ 29/516 |
| 6,152,944 A | * | 11/2000 | Holman et al. ............. 606/194 |
| 6,432,130 B1 | * | 8/2002 | Hanson ..................... 623/1.11 |

FOREIGN PATENT DOCUMENTS

EP  1 018 320 A  7/2000

* cited by examiner

*Primary Examiner*—Bruce E Snow
(74) *Attorney, Agent, or Firm*—Vidas, Arrett & Steinkraus, P.A.

(57) ABSTRACT

A protective sleeve for a catheter assembly comprising a tubular member composed of a first material. The first material having a first predetermined modulus of elasticity. The tubular member having at least one stripe of a second material engaged thereto. The second material having a greater modulus of elasticity than the first material. The tubular member having a loading state and being crimpable to a reduced state. In the loading state the tubular member being sized to disposingly engage the balloon of a catheter assembly wherein the balloon has a first diameter. When the tubular member is in the reduced state the tubular member is disposingly and retainingly engaged to the balloon. When the tubular member is in the reduced state the balloon has a second diameter which is less than the first diameter.

15 Claims, 5 Drawing Sheets

CRIMPABLE BALLOON/STENT PROTECTOR

CROSS-REFERENCE TO RELATED APPLICATIONS

Not Applicable

STATEMENT REGARDING FEDERALLY SPONSORED RESEARCH

Not Applicable

BACKGROUND OF THE INVENTION

1. Field of the Invention

The present invention relates generally to catheters having an expandable balloon and to premounted balloon expandable stent balloon catheters generally. More specifically, the present invention is directed to dilatation balloon catheters having a removable protective sheath which may reduce potential trauma caused to the stent and/or the balloon during a crimping process.

2. Description of Related Art

Percutaneous transluminal coronary angioplasty (PTCA) is a procedure which is well established for the treatment of blockages in the coronary arteries. Blockages may occur from cholesterol precipitation on the coronary wall which may be in any stage from initial deposit through aged lesions. Coronary arteries may also become blocked due to formation of thrombus.

The most widely used form of percutaneous coronary angioplasty makes use of a dilatation balloon catheter. In typical PTCA procedures, the cardiovascular system of a patient is accessed with an introducer, usually in the groin area. All other devices including a guiding catheter are percutaneously introduced into the cardiovascular system of a patient through the introducer and advanced through a vessel until the distal end thereof is at a desired location in the vasculature. A guide wire and a dilatation catheter having a balloon on the distal end thereof are introduced through the guiding catheter with the guide wire sliding through the dilatation catheter. The guide wire is first advanced out of the guiding catheter into the patient's coronary vasculature and the dilatation catheter is advanced over the previously advanced guide wire until the dilatation balloon is properly positioned across the lesion. Once in position across the lesion, the flexible, expandable, preformed balloon is inflated to a predetermined size with a fluid at relatively high pressures, such as greater than about four atmospheres, to radially compress the atherosclerotic plaque of the lesion against the inside of the artery wall and thereby dilate the lumen of the artery. The balloon is then deflated to a small profile so that the dilatation catheter may be withdrawn from the patients vasculature and blood flow resumed through the dilated artery.

In angioplasty procedures of the kind described above, there may be restenosis of the artery, which either necessitates another angioplasty procedure, a surgical by-pass operation, or some method of repairing or strengthening the area. To reduce restenosis and strengthen the area, a physician can implant an intravascular prosthesis for maintaining vascular patency, called a stent, inside the artery at the lesion. In general, stents are prosthetic devices which can be positioned within a body cavity, for example, a blood vessel of the body of a living human or in some other difficulty accessible place. A stent generally has a diameter which may be increased or decreased. Stents are particularly useful for permanently widening a vessel which is in a narrowed state, or for internally supporting a vessel damaged by an aneurysm.

Such stents are typically introduced into the body cavity by use of a catheter. The catheter is usually of the balloon catheter type in which the balloon is utilized to expand the stent, which is positioned over the balloon, to place it in a selected location in the body cavity. The stent is expanded to a larger diameter for placement in the vasculature, often by the balloon portion of the catheter. Stents delivered to a restricted coronary artery, expanded to a larger diameter by a balloon catheter, and left in place in the artery at the site of a dilated lesion are shown in U.S. Pat. No. 4,740,207 to Kreamer and U.S. Pat. No. 5,007,926 to Derbyshire.

In advancing an inflation expandable balloon through a body vessel to the deployment site, the stent must be able to securely maintain its axial position on the delivery catheter, without trans-locating proximally or distally, and especially without becoming separated from the catheter. Stents that are not properly secured or retained to the catheter may slip and either be lost or be deployed in the wrong location or partially deployed. In securing a stent to a catheter, however, the stent must be crimped in such a way as to minimize or prevent altogether distortion of the stent and to thereby prevent abrasion and/or reduce trauma of the vessel walls.

In the past, crimping and balloon reduction has been done by hand often resulting in the application of undesired uneven forces to the stent. Such a stent must either be discarded or re-crimped. Stents which have been crimped multiple times can suffer from fatigue and may be scored or otherwise marked which can cause thrombosis. A poorly crimped stent can also damage the underlying balloon.

Recently, stent crimping devices have been disclosed in U.S. Pat. No. 5,546,646 to Williams et al, U.S. Pat. No. 5,183,085 to Timmermans et al., U.S. Pat. No. 5,626,604 to Cottone, Jr., U.S. Pat. No. 5,725,519, to Penner et al., U.S. Pat. No. 5,810,873 to Morales, WO 97/20593, WO 98/19633 and copending U.S. application Ser. No. 09/404,986, filed Sep. 22, 1999 to Klisch et al, the entire contents of each reference being respectively incorporated herein by reference.

One important characteristic of a dilatation balloon catheter as well as a stent delivery catheter is its "profile", which is determined by the outer diameter (O.D.) of the distal end portion of the balloon and stent when deflated. The outer diameter affects the ease and ability of the dilatation catheter to pass through a guide catheter, through the coronary arteries, and across a lesion. Considerable effort has been made in developing low profile dilatation balloon catheters. U.S. Pat. No. 5,342,307, incorporated herein by reference, discloses a balloon protector sleeve used with a ti-fold dilatation balloon catheter for angioplasty. Because reduction of profile is of significance balloon reduction often includes the use of a first profile reducing "bi-tube" as well as one or more smaller balloon protectors. Typically the bi-tube is placed about the balloon after the balloon is folded and wrapped. The bi-tube is typically removed and replaced with one or more balloon protectors suitable for retaining the balloon in the reduced configuration for shipment or storage. Such use of bi-tubes and balloon protectors are also used in prior stent crimping processes as will be described in greater detail below.

Minimization of "profile" is of importance in balloon catheters and stent delivery systems. In addition to securing the stent onto the balloon catheter, the crimping process may also provide the catheter with a reduced profile configuration. Accordingly, the balloon protector of the present invention is particularly directed for use with balloon catheters and stent delivery systems wherein the protector provides the balloon and stent with protection during the crimping process, thereby allowing the stent to be safely secured to the balloon in a reduced profile state.

All U.S. patents, applications and all other published documents mentioned anywhere in this application are incorporated herein by reference in their entirety.

BRIEF SUMMARY OF THE INVENTION

This invention is directed to a crimpable sheath or protector which may be placed onto the balloon carrying portion of a catheter or stent delivery system prior to reduction of the balloon and/or crimping of a stent onto the balloon. The invention eliminates direct contact between the crimping apparatus and the stent and/or balloon. The larger size and potential surface area of the protector allows for minimization of loading forces and allows the catheter to achieve an optimum profile while minimizing trauma to the underlying balloon and/or stent.

In at least one embodiment of the invention, the inventive balloon protector may be characterized as a polymer sleeve or tube which includes at least one fiber or stripe of relatively rigid material embedded into the polymer material. The fiber or fibers may be configured and oriented in any manner. For example: the fiber(s) may be longitudinally, radially, and/or helically, oriented relative to the longitudinal axis of the protector. The fibers may also be braided together to form a net like configuration. The fiber may be uniformly dispersed throughout the protector body or may be configured with a variety of uniform or non-uniform patterns of dispersion as may be desired.

In at least one embodiment of the invention, the protector is employed with a catheter having an expandable distal portion constructed and arranged for expanding the outer diameter of the catheter from a contracted state to an expanded state. The distal portion of the catheter comprises a balloon which is folded or otherwise collapsed, and is expandable to an expanded condition. The balloon protector may comprise a removable sleeve.

In at least one embodiment of the invention, the sleeve is constructed from at least two materials, wherein the second material is characterized as one or more strands of a rigid material or braids of relatively hard material suspended within or by the first material.

A description of the manufacture of a type of dual material sleeve may be found in U.S. patent application Ser. No. 09/668,496, filed Sep. 22, 2000, to Yang as well as in the related U.S. patent application Ser. No. 09/716,757, filed Nov. 20, 2000, the entire contents of both references being incorporated herein by reference.

The inside diameter of the protector is sized to allow for minimal loading force thereby allowing for ready insertion of the distal end of the balloon catheter into the protector. Because the protector is suitable for use with virtually any size of balloon catheter the inner diameter may range from 0.5 mm to over 10.00 mm if desired. However, typically the protector will have an inner diameter of 0.75 mm to about 5.0 mm.

In use the protector sleeve is positioned around the balloon, and optionally over a stent, prior to reduction of the balloon or crimping of the stent onto the balloon surface. Alternatively, the stent may also be loaded onto a reduced balloon after the protector has been placed thereon. The combined balloon/protector apparatus may then be inserted into a stent crimping apparatus such as those described in the references cited above. Other crimping devices which may be used include but are not limited to the TOMINATOR™ crimping device available from Machine Solutions of Flagstaff, Ariz.

The protector prevents direct contact between the crimping apparatus and the balloon as well as the stent. By preventing direct contact between the crimper and stent, the protector of the present invention allows stents having relatively fragile stent coatings, such as are known to be used in drug delivery applications to be crimped onto a balloon without causing damage to the stent or the relatively delicate coatings. Some examples of stents have drug delivery coatings are described in U.S. Pat. No. 5,972,027 and copending U.S. application Ser. No. 09/420,094, filed Oct. 18, 1999 to Johnson, the entire contents of both of which being incorporated herein by reference.

After reduction or crimping of the catheter and protector, the protector provides a compressive force to retain the balloon in a reduced configuration. The protective sleeve is removed from the catheter prior to use of the catheter.

The present invention also provides for an improved process for applying a balloon protector by providing a crimpable balloon protector which does not require the use of a bi-tube for initial balloon preparation. As may be known, the application of many prior balloon protectors require several steps. For example, applying a prior balloon protector may require the following steps: Loading the bi-tube onto the shaft the of a balloon catheter, then folding the balloon into a desired configuration followed by wrapping the folded balloon. The bi-tube is then slid over the wrapped balloon. Next, the balloon and bi-tube are heat set during the curing process of the shaft coating of the catheter. Following the heat set process, the bi-tube is removed from the balloon and a the smaller diameter balloon protector is placed over the balloon in order to improve profile and to protect the balloon during shipment and storage.

By providing a crimpable balloon protector as described herein, the present invention eliminates the need for a bi-tube and thus the process steps associated with the bi-tube.

In at least one embodiment of the invention the, the invention provides for an improved method for applying the present balloon protector to a balloon. At least one embodiment of the inventive method includes applying the present balloon protector to a formed balloon. The combined balloon and protector is then crimped. The crimping action reduced the profile of the balloon and simultaneously wraps the balloon. The combination balloon and protector is now in condition for shipment and/or storage. The protector remains on the balloon until the balloon is ready for use.

Similar to the process for applying a prior type of balloon protector, prior systems of crimping a stent onto a balloon and applying a stent protector often require numerous steps. For example, a application of a stent protector may require the following steps: folding the balloon, wrapping the balloon, sliding the bi-tube over the balloon, heat setting the balloon, loading the stent onto the balloon, crimping the stent, and finally loading a stent protector over the stent. By providing a crimpable stent protector, the present invention provides a stent protector which may be placed over the stent prior to crimping. As a result, the stent is protected during the crimping process as the blades of the crimper are not able to directly.

In at least one embodiment of the invention a first crimpable balloon protector may be applied to a balloon as described above. After crimping the balloon and protector, the balloon protector is removed from the balloon and a stent is loaded onto the balloon. A a crimpable stent protector may then be placed over the stent. The entire apparatus is then crimped. The crimpable stent protector is removed prior to use of the stent delivery catheter.

In at least one embodiment of the invention the protective sleeve may have one or more slits along its length such as are described in U.S. Pat. No. 6,152,944.

In at least one embodiment of the invention the protective sleeve may include one or more longitudinally oriented indentations or grooves. These indentations may be characterized as scoring on the inside, outside or both surfaces of the protector. The presence of scoring provides additional flexibility to the protector and allows the protector to be reduced in diameter, such as is caused by the crimping process, without distorting the general shape of the protector. The indentations may extend across the entire length of the protector and may have a variety of shapes and configurations.

BRIEF DESCRIPTION OF THE SEVERAL VIEWS OF THE DRAWINGS

A detailed description of the invention is hereafter described with specific reference being made to the drawings in which.

DETAILED DESCRIPTION OF THE INVENTION

Figure 1:
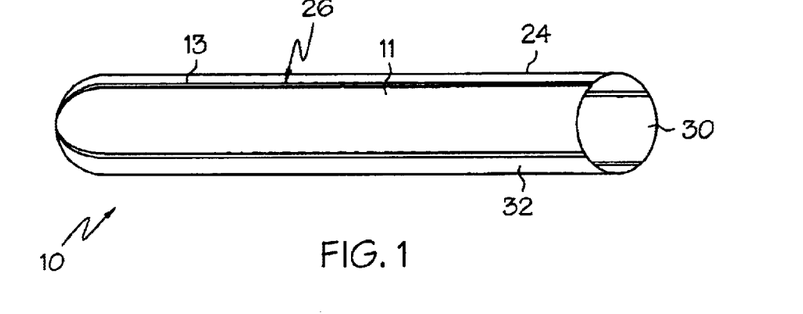
FIG. 1 is a perspective view of an embodiment of the invention.

As may be seen in FIG. 1, the present invention is directed to a balloon/stent protector 10 which has a composite construction of at least two materials. The protector sleeve 10 may be composed of a first polymeric material 11 which may be any flexible polymeric material such as PE, PTFE, Nylon, Teflon, polyamide, and/or other suitable polymer material. Other materials form which the first material 11 may be selected include, but are not limited to: polyurethane-polyether polymers, such as Tecothane™ available from Thermedics, Inc.; polyester-polyurethanes, such as Pellethane™ sold by Dow Chemical; polyether-polyurethanes, such as Estane™ sold by BF Goodrich; polyether block amides, such as Pebax™ available from Elf Atochem; and styrene-butadien-styrene triblock copolymers such as Kraton™ sold by Shell Chemical company. Other materials which may also be used in the production of the first material 11 include, but are not limited to styrenic block copolymers, polyurethanes, silicone rubber, natural rubber, copolyesters, polyamides, EPDM rubber/polyolefin, nitril rubber/PVC, fluoroelastomers, butyl rubber, epichlorohydrin, polyethylene, high density polyethylene (HDPE), and any combinations thereof. Alternatively, the first material may also be woven fabric or mesh.

The first material 11 has one or more strands of a second material 13 which is characterized as having a greater modulus of elasticity than the first material 11 imbedded or coextruded therewith. The second material 13 may be a polymer of a relatively hard nature when compared to the first material 11. The second material 13 may be selected from one or more of the following substances: metal, glass, carbon, and/or polymers.

Where the material 13 includes a polymer, such polymer materials may be a liquid crystal polymer (LCP) such as VECTRA®, polyetheretherketone (PEEK) material, and PPS. Other materials may also be utilized as the fibril component of the present invention. Such substances include aromatic nylon, rigid polyurethane, polyester, copolyester, polyester blends, polyester/polyurethane blends, PEEK, PPS, fluoropolymer and so on.

The material 13 may be characterized as a fiber and may include one or more of the following substances: polyurethane-polyether polymers, such as Tecothane™ available from Thermedics, Inc.; polyether-polyurethanes, such as Estane™ sold by BF Goodrich; polyether block amides, such as Pebax™ available from Elf Atochem. Other materials which may also be used in the production of the second material 13 include, but are not limited to: polyolefins, polystyrene, polyvinyl chloride, acrylonitrile-butadiene-styrene polymers, polyacrylonitrile, polyacrylate, vinyl acetate polymer, cellulose plastics, polyurethanes, polyethylene terephthalate, polyacetal, polyethers, polycarbonates, polyamides, polyphenylene sulfide, polyarylethersulfones, polyaryletherketones, polytetrafluoroethylene, and any combinations thereof.

Other materials which may be suitable for use in forming the fiber material 13 include Nylon; Kevlar™; polyethyleneterephthalate (PET); metals such as: stainless steel, aluminum, NITINOL and others. Other embodiments include the use of glass filled nylon and woven fabric or mesh. In addition, the second material 13, may be a combination of relatively hard materials. For example, the second material 13 may be a woven braid of multiple materials such as, NITINOL and stainless steel.

Figure 2:
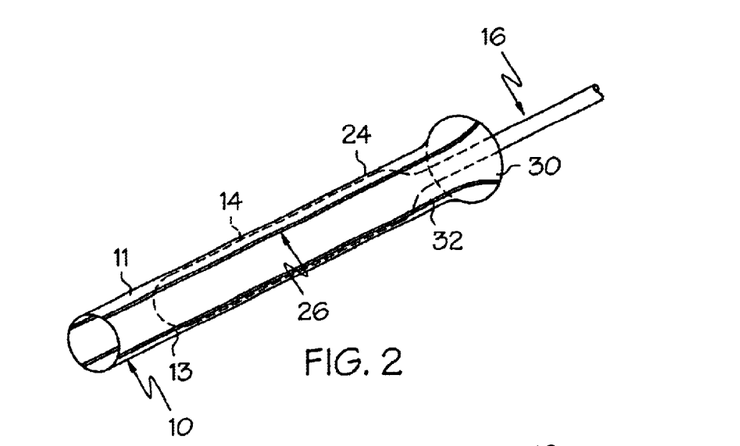
FIG. 2 is a perspective view of the embodiment of the invention shown in FIG. 1 mounted an a catheter.
Figure 3:
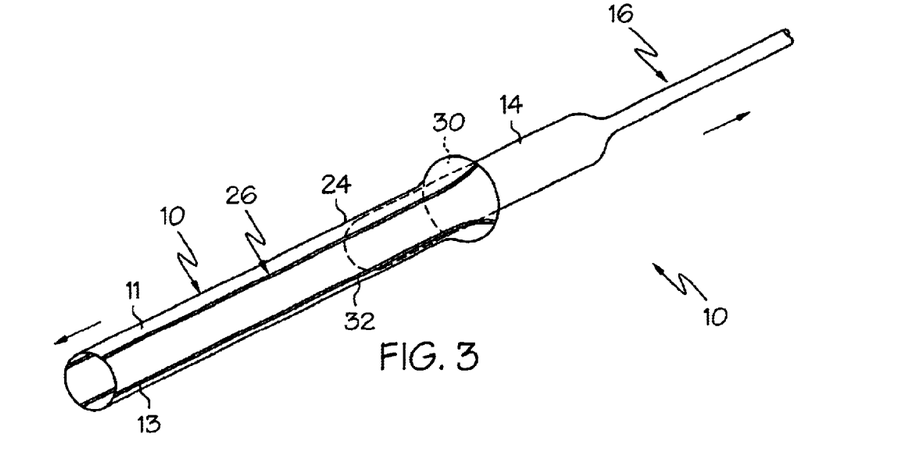
FIG. 3 is a perspective view of the embodiment of the invention shown in FIG. 1, wherein the protector is shown being removed from the catheter.

As depicted in FIG. 2, the unique construction of the protector 10 allows the protector 10 to be placed about the balloon portion 14 of a catheter 16 and may then be subjected to crimping forces. Despite being crimped around the balloon 14, the protector 10 may be removed from the balloon 14 prior to insertion of the catheter 16 into a body lumen, such as is shown in FIG. 3.

Figure 4:
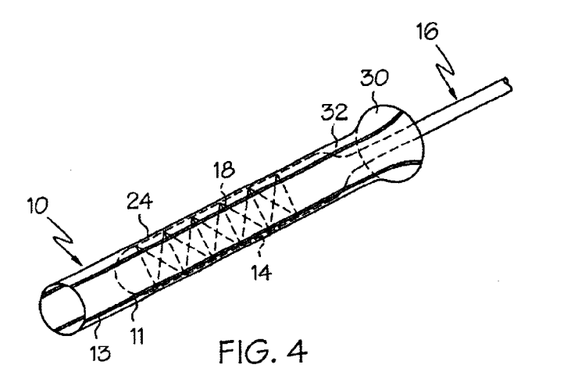
FIG. 4 is a perspective view of the embodiment of the invention shown in FIG. 1 mounted an a catheter, wherein the catheter includes a stent.
Figure 5:
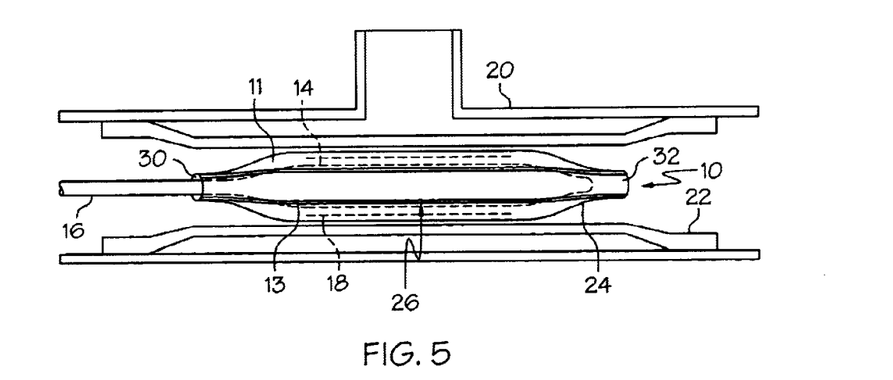
FIG. 5 is a perspective view of the embodiment shown in FIG. 4 wherein the protector and catheter are shown being crimped.

As may be seen in FIG. 4, the present protector 10 may also be utilized to crimp a stent 18 onto a balloon 14 of the catheter 16. The protector 10 is placed over the stent 18 before the stent is crimped. As may be seen in FIG. 5, the combination of the catheter 16, stent 18 and protector 10 is inserted into a crimping device 20. The crimping forces are transmitted to the stent 18 but the crimping blades 22 are prevented from contacting the stent 18 due to the presence of the protector 10. The protector 10 may be removed from the catheter 16 at any time after the crimping process.

As previously indicated, the protector 10 is constructed from at least two materials having different modulus of elasticity. The first material 11 is formed into a generally tubular sleeve 24. In the embodiment shown in FIGS. 1–5, the second material 13 is embodied in at least one fiber or stripe of material 26. In the embodiment shown, the fiber 26 is substantially parallel to the longitudinal axis 25 of the protector 10.

As indicated above, the first material 11 may be any elastic material known. The first material 11 has a modulus of elasticity less than that of the second material 13. The second material 13 may be any material that when presented as one or more longitudinally oriented fibers has a modulus of elasticity greater than that of the first material 11.

Figure 12:
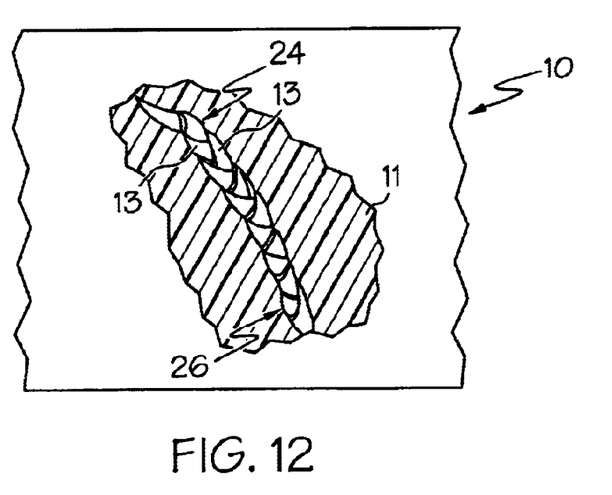
FIG. 12 is a detailed partially cut-away view of a portion of the protector shown in the embodiments of FIGS. 1–5.

The various substances which may be used to form the second material 13 may be used singly or be combined in a wide variety of manners and configurations. Where the second material 13 is embodied as one or mote fibers 26 such as is shown in FIGS. 1–5, each fiber 25 may be a combination of one or more materials 13 that maybe woven or braided together to form a braid 29, such as is shown in FIG. 12, or a single continuous shaft of material or materials such as a filament, wire or ribbon of one or more of the materials 13 mentioned above. Other configurations may also be provided, some of which are described in greater detail below.

In addition, the manner in which the fiber(s) 26 are combined with the first material 11 may also vary. The fiber(s) 26 may be co-extruded with the first material 11. The fiber(s) 26 may be imbedded into the first material 11, or may be placed over the first material 11. The fiber(s) 26 may also be woven into the matrix of the first material 11.

The above examples of the combining of the first and second materials 11 and 13 or the configurations of fiber(s) 26 or the various manners in which the fiber(s) 26 and first material 11 may be joined, are in no way exhaustive of the potential substances or combinations of substances which may be used. The present invention is directed to a sleeve 24 composed of any materials which have the respective modulus of elasticity qualities previously described for the respective materials 11 and 13.

As may be seen in the various figures, the present invention may be embodied in a variety of manners. For instance, in the embodiment shown in FIG. 1 the protector 10 is shown with a plurality of substantially parallel longitudinally oriented fibers 26.

Figure 6:
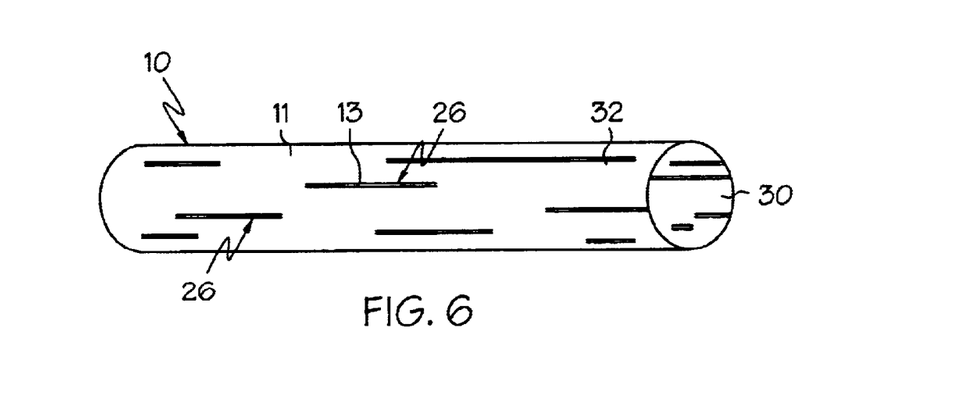
FIG. 6 is a perspective view of an alternative embodiment of the invention.

As may be seen in FIG. 6, the fibers 26 do not necessarily extend over the entire length of the protector 10. In addition, the fibers 26 may be configured to have a variety of lengths, and may be spaced uniformly or non-uniformly through out the first material 11.

Figure 7:
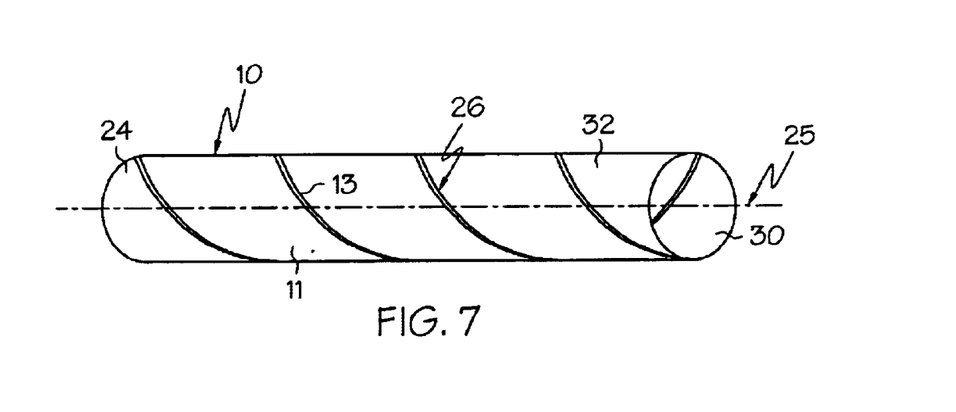
FIG. 7 is a perspective view of an alternative embodiment of the invention.

In FIG. 7 an embodiment of the invention is shown wherein the second material 13 is distributed in a plurality of fibers 26 which have a helical distribution about the sleeve 24 relative to the longitudinal axis 25.

Figure 8:
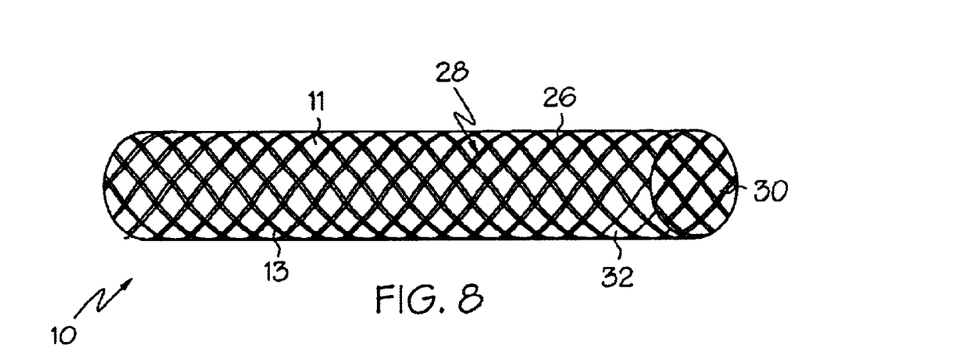
FIG. 8 is a perspective view of an alternative embodiment of the invention.

In FIG. 8 the protector 10 is shown wherein the first material 11 is of a single uniform construction and the second material 13 is comprised of a web 28 of interconnecting fibers 26 embedded therein.

In all of the various embodiments of the invention depicted and/or described herein the protector 10 may be characterized as having an inside surface 30 and an outside surface 32. The inner and/or outer surfaces 30 and 32 may be entirely or selectively coated with a lubricious coating such as may be known. The use of such a coating may provide the protector with the ability to be more readily retracted off of the stent 18 and or balloon 14.

As indicated above, the present balloon protector may be utilized for balloon reducing processes as well as stent crimping procedures. Where the protector is used to reduce a balloon the protector may be placed directly over a folded balloon. The protector and balloon may then be crimped which acts to wrap the balloon. If the balloon is to include a stent, the crimped protector may be removed and the stent loaded into place. A second protector is inserted over the stent and balloon and the entire assembly is then crimped.

Figure 9:
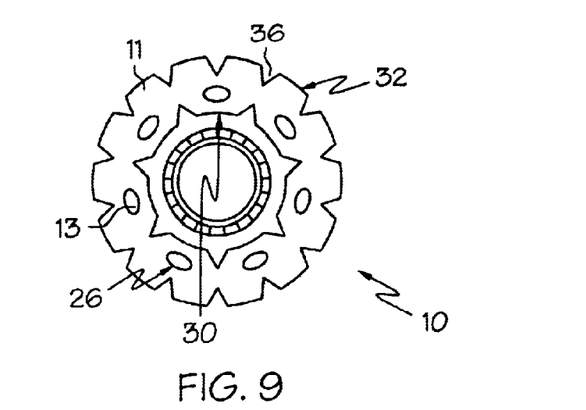
FIG. 9 is a cross-sectional view of an alternative embodiment of the invention.
Figure 10:
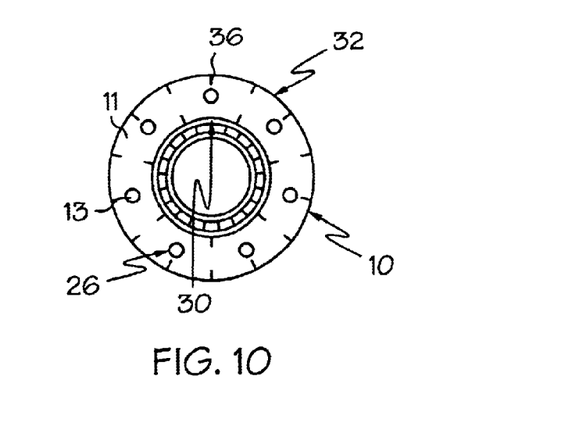
FIG. 10 is a cross-sectional view of the embodiment shown in FIG. 9, wherein the protector is shown in a reduced configuration.

Whether the protector 10 is utilized for balloon reduction and/or stent crimping, the protector 10 is capable of uniformly transmitting crimping forces to the balloon 16 and/or stent 18. As may be seen in FIG. 9 the outside surface 32 of the protector 10 is equipped with a plurality of longitudinally oriented channels or scoring marks 36 which provide the protector 10 with the ability to collapse in a uniform manner. In the present embodiment the marks 36 are scored out of the more flexible first material 11 so that when the protector 10 is reduced by being crimped, the channels 36 close up upon themselves thereby reducing the diameter of the protector 10 in a substantially uniform manner such as is shown in FIG. 10. The channels 36 may be on the outside surface 32 and/or the inside surface 30 as desired.

Figure 11:
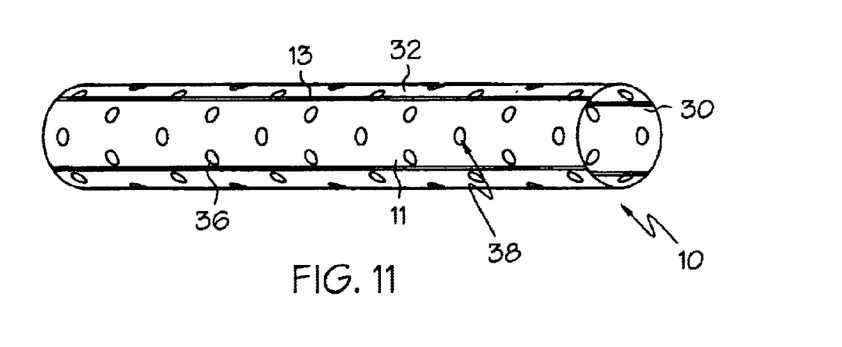
FIG. 11 is a perspective view of an alternative embodiment of the invention.

In an alternative embodiment shown in FIG. 11, the marks 36 are characterized as dimples or pores 38. When the protector 10 is in the reduced state described above, the dimples 38 will close up in a similar manner.

In addition to being directed to the embodiments described above and claimed below, the present invention is further directed to embodiments having different combinations of the features described above and claimed below. As such, the invention is also directed to other embodiments having any other possible combination of the dependent features claimed below.

The above examples and disclosure are intended to be illustrative and not exhaustive. These examples and description will suggest many variations and alternatives to one of ordinary skill in this art. All these alternatives and variations are intended to be included within the scope of the attached claims. Those familiar with the art may recognize other equivalents to the specific embodiments described herein which equivalents are also intended to be encompassed by the claims attached hereto.

What is claimed is:

1. A catheter assembly having a protected configuration and a delivery configuration, the catheter comprising:

a balloon, the balloon having a length;

a stent, the stent being disposed about at least a portion of the balloon; and     a protective sleeve, in the protected configuration the protective sleeve being disposed about the entire length of the stent and balloon, in the delivery configuration the protective sleeve being removed from the balloon, the protective sleeve comprising:

a tubular member having a longitudinal axis composed of a first material, wherein the first material has a first predetermined modulus of elasticity, the tubular member having at least one stripe of a second material engaged thereto, the second material having a second predetermined modulus of elasticity, the second predetermined modulus of elasticity being greater than the first predetermined modulus of elasticity, the at least one stripe being substantially parallel to the longitudinal axis of the tubular member, in the protected configuration the tubular member having a loading state and being crimpable to a crimped state, in the loading state the tubular member having a first diameter, in the crimped state the tubular member having a second diameter, the second diameter being less than the first diameter, in the crimped state the tubular member retaining the balloon in a reduced profile configuration, in the delivery configuration the tubular member being removed from the balloon while in the crimped state prior to insertion of the catheter assembly into a body lumen.

2. The catheter assembly of claim 1 wherein the at least one stripe is embedded in the first material.

3. The catheter assembly of claim 1 wherein the first material further comprises a plurality of scoring marks, when the tubular member is crimped from the lading state to the crimped state the scoring marks constructed and arranged to collapse upon themselves.

4. The catheter assembly of claim 3 wherein the plurality of scoring marks are characterized as a plurality of channels.

5. The catheter assembly of claim 4 wherein the tubular member further comprises an inside surface and an outside surface.

6. The catheter assembly of claim 3 wherein the plurality of scoring marks are characterized as a plurality of pores.

7. The catheter assembly of claim 1 wherein the first material is constructed from at least one member of the group consisting of styrenic block copolymers, polyurethanes, silicone rubber, natural rubber, copolyesters, polyamides, EPDM rubber/polyolefin, nitril rubber/PVC, fluoroelastomers, butyl rubber, epichlorohydrin, polyethylene, high density polyethylene and any combinations thereof.

8. The catheter assembly of claim 1 wherein the second material is at least partially compose of at least one member of the group consisting of: liquid crystal polymers, polyester, copolyester, polyester blends, PEEK, PPS, fluoropolymers, polyether block amides, polyolefins, polystyrene, polyvinyl chloride, acrylonitrile-butadiene-styrene polymers, polyacrylonitrile, polyacrylate, vinyl acetate polymer, cellulose plastics, polyurethanes, polyethylene terephthalate, polyacetal, polyethers, polycarbonates, polyamides, polyphenylene sulfide, polyarylethersulfones, polyaryletherketones, polytetrafluoroethylene, polyethyleneterephthalate, nylon, metal, carbon, glass, fabric and any combinations thereof.

9. The catheter assembly of claim 8 wherein the second material comprises a braid of Nitinol and stainless steel.

10. The catheter assembly of claim 8 wherein the first material and the second material are co-extruded.

11. The catheter assembly of claim 8 wherein the at least on stripe is a wire, the wire engaged to the first material.

12. The catheter assembly of claim 8 wherein the at least stripe comprises a plurality of stripes.

13. The catheter assembly of claim 12 wherein the plurality of stripes are distributed uniformly about the tubular member.

14. The protective sleeve of claim 12 wherein the plurality of stripes are randomly dispersed about the tubular member.

15. The catheter assembly of claim 1 wherein the tubular member further comprises an inside surface and an outside surface, at least one of the inside and outside surfaces having a lubricious coating thereon.

* * * * *